United States Patent [19]

Weber

[11] Patent Number: 5,130,120
[45] Date of Patent: Jul. 14, 1992

[54] PARAMAGNETIC DTPA AND EDTA ALKOXYALKYLAMIDE COMPLEXES AS MRI AGENTS

[75] Inventor: Robert W. Weber, Downingtown, Pa.

[73] Assignee: Mallinckrodt Medical, Inc., St. Louis, Mo.

[21] Appl. No.: 221,425

[22] Filed: Jul. 19, 1988

[51] Int. Cl.$^5$ .................. A01N 24/00; C01N 31/00; C07F 5/00; C07F 13/00
[52] U.S. Cl. ........................................ 424/9; 514/492; 514/836; 436/173; 534/16; 556/45; 556/57; 556/110; 556/138
[58] Field of Search ............... 424/9; 514/558, 563, 514/974, 492, 836; 556/45, 57, 110, 138; 436/173; 534/16; 128/654, 653 CA, 653 AF

[56] References Cited

U.S. PATENT DOCUMENTS

| | | | |
|---|---|---|---|
| 4,647,447 | 3/1987 | Gries et al. | 424/9 |
| 4,687,659 | 8/1987 | Quay | 424/9 |
| 4,826,673 | 5/1989 | Dean et al. | 424/9 |
| 4,957,939 | 9/1990 | Gries et al. | 514/492 |
| 4,963,344 | 10/1990 | Gries et al. | 424/9 |

FOREIGN PATENT DOCUMENTS 0263059  4/1988  European Pat. Off. .

Primary Examiner—Glennon H. Hollrah
Assistant Examiner—Gary E. Hollinden
Attorney, Agent, or Firm—Rothwell, Figg, Ernst & Kurz

[57] ABSTRACT

Novel magnetic resonance imaging agents and methods which utilize complexes of paramagnetic ions with alkoxyalkylamide derivatives of diethylenetriaminepentaacetic acid ("DTPA") or ethylenediaminetetraacetic acid ("EDTA"). These novel imaging agents are characterized by excellent NMR image-contrasting properties and by high solubilities in physiological solutions. The complexes are represented by the following formula:

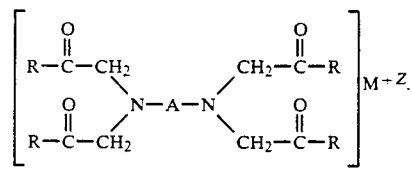

wherein A is —CH$_2$CH$_2$— or

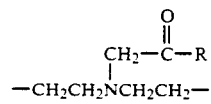

and M$^{+z}$ is a paramagnetic ion of an element with an atomic number of 21-29, 42-44 or 58-70, and a valence, Z, of 2 or 3; the R groups may be the same or different and are selected from the group consisting of —O$^\ominus$ and lower alkoxyalkylamino groups having from 2 to about 6 carbon atoms, wherein the number of R groups —O$^\ominus$ equals Z and the remaining R groups are lower alkoxyalkylamino, equal to 4-Z when A is —CH$_2$CH$_2$—, or 5-Z when A

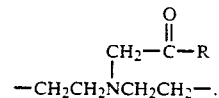

41 Claims, No Drawings

PARAMAGNETIC DTPA AND EDTA ALKOXYALKYLAMIDE COMPLEXES AS MRI AGENTS

BACKGROUND OF THE INVENTION

This invention relates to nuclear magnetic resonance (NMR) imaging and, more particularly, to methods and compositions for enhancing NMR imaging.

The recently developed technique of NMR imaging encompasses the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. As currently used, the images produced constitute a map of the distribution density of protons and/or their relaxation times in organs and tissues. The technique of NMR imaging is advantageously non-invasive as it avoids the use of ionizing radiation.

While the phenomenon of NMR was discovered in 1945, it is only relatively recently that it has found application as a means of mapping the internal structure of the body as a result of the original suggestion of Lauterbur (*Nature*, 242, 190-191 (1973)). The fundamental lack of any known hazard associated with the level of the magnetic and radio-frequency fields that are employed renders it possible to make repeated scans on vulnerable individuals. Additionally, any scan plane can readily be selected, including transverse, coronal and sagittal sections.

In an NMR experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin, when placed in an applied magnetic field (B, expressed generally in units of gauss or Tesla ($10^4$ gauss)) align in the direction of the field. In the case of protons, these nuclei precess at a frequency, f, of 42.6 MHz at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In NMR imaging, scanning planes and slice thicknesses can be selected. This selection permits high quality transverse, coronal and sagittal images to be obtained directly. The absence of any moving parts in NMR imaging equipment promotes a high reliability. It is believed that NMR imaging has a greater potential than CT for the selective examination of tissue characteristics in view of the fact that in CT, x-ray attenuation coefficients alone determine image contrast, whereas at least four separate variables ($T_1$, $T_2$, proton density and flow) may contribute to the NMR signal. For example, it has been shown (Damadian, *Science*, 171, 1151 (1971)) that the values of the $T_1$ and $T_2$ relaxation in tissues are generally longer by about a factor of 2 in excised specimens of neoplastic tissue compared with the host tissue.

By reason of its sensitivity to subtle physicochemical differences between organs and/or tissues, it is believed that NMR may be capable of differentiating different tissue types and in detecting diseases which induce physicochemical changes that may not be detected by x-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei (e.g., viscosity, temperature, and the like). These two relaxation phenomena are essentially mechanisms whereby the initially imparted radiofrequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment within which it finds itself.

In general, paramagnetic divalent or trivalent ions of elements with an atomic number of 21 to 29, 42 to 44 and 58 to 70 have been found effective as NMR image contrasting agents. Suitable such ions include chromium (III), manganese (II), manganese (III), iron (III), iron (II), cobalt (II), nickel (II), copper (II), praseodymium (III), neodymium (III), samarium (III) and ytterbium (III). Because of their very strong magnetic moments, gadolinium (III), terbium (III), dysprosium (III), holmium (III) and erbium (III) are preferred. Gadolinium (III) ions have been particularly preferred as NMR image contrasting agents.

Typically, the divalent and trivalent paramagnetic ions have been administered in the form of complexes with organic complexing agents. Such complexes provide the paramagnetic ions in a soluble, non-toxic form, and facilitate their rapid clearance from the body following the imaging procedure. Gries et al., U.S. Pat. No. 4,647,447, disclose complexes of various paramagnetic ions with conventional aminocarboxylic acid complexing agents. A preferred complex disclosed by Gries et al. is the complex of gadolinium (III) with diethylenetriaminepentaacetic acid ("DTPA"). This complex may be represented by the formula:

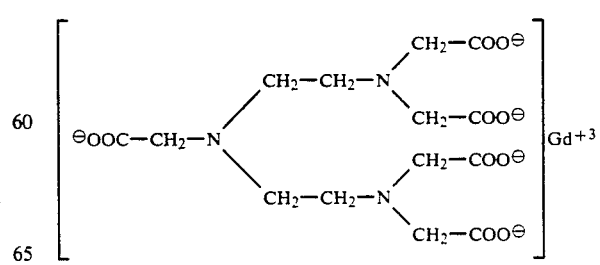

Paramagnetic ions, such as gadolinium (III), have been found to form strong complexes with DTPA.

These complexes do not dissociate substantially in physiological aqueous fluids. The complexes have a net charge of −2, and generally are administered as soluble salts. Typical such salts are the sodium and N-methylglucamine salts.

The administration of ionizable salts is attended by certain disadvantages. These salts can raise the in vivo ion concentration and cause localized disturbances in osmolality, which in turn, can lead to edema and other undesirable reactions.

Efforts have been made to design non-ionic paramagnetic ion complexes. In general, this goal has been achieved by converting one or more of the free carboxylic acid groups of the complexing agent to neutral, non-ionizable groups. For example, S.C. Quay, in U.S. Pat. Nos. 4,687,658 and 4,687,659, discloses alkylester and alkylamide derivatives, respectively, of DTPA complexes. Similarly, published West German applications P 33 24 235.6 and P 33 24 236.4 disclose mono- and polyhydroxyalkylamide derivatives of DTPA and their use as complexing agents for paramagnetic ions.

The nature of the derivative used to convert carboxylic acid groups to non-ionic groups can have a significant impact on solubility. For example, derivatizing the carboxylic acid groups with hydrophobic alkylamide groups substantially decreases the water solubility of the complex. The solubility of the complexes in physiological fluids can, in turn, affect the tissue selectivity of the complex. Hydrophilic complexes tend to concentrate in the interstitial fluids, whereas hydrophobic complexes tend to associate with cells. Thus, differences in hydrophilicity can lead to different applications of the compounds. See, for example, Weinmann et al., AJR, 142, 679 (Mar. 1984) and Brasch et al., AJR, 142, 625 (Mar. 1984).

Thus, a need continues to exist for new and structurally diverse non-ionic complexes of paramagnetic ions for use as NMR imaging agents.

SUMMARY OF THE INVENTION

The present invention provides novel complexing agents and complexes of complexing agents with paramagnetic ions. The complexes are represented by the following formula:

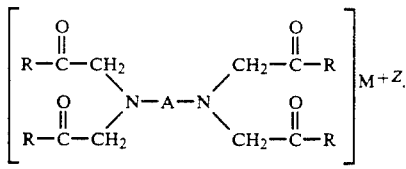

wherein A is —CH$_2$CH$_2$— or

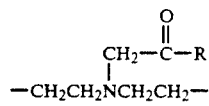

and M$^{+z}$ is a paramagnetic ion of an element with an atomic number of 21-29, 42-44 or 58-70, and a valence, Z, of +2 or +3; the R groups may be the same or different and are selected from the group consisting of —O$^⊖$ and lower alkoxyalkylamino groups having from 2 to about 6 carbon atoms, wherein Z of the R groups are —O$^⊖$ and 5-Z of the R groups are lower alkoxyalkylamino groups.

Also disclosed is a method of performing an NMR diagnostic procedure which involves administering to a warm-blooded animal an effective amount of the above-described complex and then exposing the warm-blooded animal to an NMR imaging procedure, thereby imaging at least a portion of the body of the warm-blooded animal.

DETAILED DESCRIPTION OF THE INVENTION

The complexing agents employed in this invention are derivatives of the well-known chelating agents, DTPA and ethylenediaminetetraacetic acid ("EDTA"). In these derivatives, free carboxylic acid groups of DTPA (those not involved in the formation of coordination bonds with the paramagnetic ion) are converted to amide groups. Thus, if the paramagnetic ion is trivalent, two of the carboxylic acid groups of DTPA or one of the carboxylic acid groups of EDTA will be derivatized to the amide form. Likewise, if the paramagnetic ion is divalent, three of the carboxylic acid groups of DTPA or two of the carboxylic acid groups of EDTA will be derivatized to the amide form. When reacted with a divalent or trivalent paramagnetic ion, the resulting complexes are substantially non-ionic and neutral.

The amide derivatives of DTPA and EDTA are prepared in a conventional manner. In general, they are prepared by reacting a stoichiometric amount of a primary lower alkoxyalkylamine with a reactive derivative of DTPA or EDTA under amide-forming conditions. Such reactive derivatives include, for example, anhydrides, mixed anhydrides and acid chlorides. In one embodiment, the reactions are conducted in an organic solvent at an elevated temperature. Suitable solvents include those in which the reactants are sufficiently soluble and which are substantially unreactive with the reactants and products. Lower aliphatic alcohols, ketones, ethers, esters, chlorinated hydrocarbons, benzene, toluene, xylene, lower aliphatic hydrocarbons, and the like may advantageously be used as reaction solvents. Examples of such solvents are methanol, ethanol, propanol, butanol, pentanol, acetone, methylethyl ketone, diethylketone, methyl acetate, ethyl acetate, chloroform, methylene chloride, dichloroethane, hexane, heptane, octane, decane, and the like. If a DTPA or EDTA acid chloride is used as the starting material, then the reaction solvent advantageously is one which does not contain reactive functional groups, such as hydroxyl groups, as these solvents can react with the acid chlorides, thus producing unwanted by-products.

The reaction temperature may vary widely, depending upon the starting materials employed, the nature of the reaction solvent and other reaction conditions. Such reaction temperatures may range, for example, from about 0° C. to about 150° C., preferably from about 30° C. to about 70° C.

Following reaction of the reactive DTPA or EDTA derivative with the lower alkoxyalkylamine, any remaining anhydride or acid chloride groups can be hydrolyzed to the carboxylate groups by adding a stoichiometric excess of water to the reaction mixture and heating for a short time.

The lower alkoxyalkylamine advantageously contains from about 2 to about 6 carbon atoms. In preferred amines, the alkoxy portion contains about 1-2 carbon atoms and the alkyl portion contains from about 2 to about 5 carbon atoms. Such amines include, for example, methoxyethylamine, methoxypropylamine, methoxybutylamine, methoxypentylamine, ethoxyethylamine, ethoxypropylamine, ethoxybutylamine, and mixtures thereof. A particularly preferred amine is methoxyethylamine.

The resulting DTPA or or EDTA alkoxyalkylamide is recovered from the reaction mixture by conventional procedures. For example, the product may be precipitated by adding a precipitating solvent to the reaction mixture, and recovered by filtration or centrifugation.

The paramagnetic ion is combined with the DTPA di- or trialkoxyalkylamide or EDTA mono- or dialkoxyalkylamide under complex-forming conditions. In general, any of the paramagnetic ions referred to above can be employed in making the complexes of this invention. The complexes can conveniently be prepared by mixing a suitable oxide or salt of the paramagnetic ion with the complexing agent in aqueous solution. To assure complete complex formation, a slight stoichiometric excess of the complexing agent may be used. In addition, an elevated temperature, e.g., ranging from about 20° C. to about 100° C., preferably from about 40° C. to about 80° C., may be employed to insure complete complex formation. Generally, complete complex formation will occur within a period from a few minutes to a few hours after mixing. The complex may be recovered by precipitation using a precipitating solvent such as acetone, and further purified by crystallization, if desired.

The novel complexes of this invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to 1.0M of a paramagnetic ion complex according to this invention. Preferred parenteral formulations have a concentration of paramagnetic ion complex of 0.1M to 0.5M. Such solutions also may contain pharmaceutically acceptable buffers and, optionally, electrolytes such as sodium chloride. The compositions may advantageously contain a slight excess, e.g., from about 0.1 to about 15 mole % excess, of the complexing agent or its complex with a physiologically acceptable, non-toxic cation to insure that all of the potentially toxic paramagnetic ion is complexed. Such physiologically acceptable, non-toxic cations include calcium ions, magnesium ions, copper ions, zinc ions and the like. Calcium ions are preferred. A typical single dosage formulation for parenteral administration has the following composition:

| | |
|---|---|
| Gadolinium DTPA-di(methoxyethylamide) | 330 mg/ml |
| Calcium DTPA-di(methoxyethylamide) | 14 mg/ml |
| Distilled Water q.s. to | 1 ml |
| pH | 7.0 |

Parenteral compositions may be injected directly or mixed with a large volume parenteral composition for systemic administration.

Formulations for enteral administration may vary widely, as is well-known in the art. In general, such formulations are liquids which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the NMR image. Such doses may vary widely, depending upon the particular paramagnetic ion complex employed, the organs or tissues which are the subject of the imaging procedure, the NMR imaging equipment being used, etc. In general, parenteral dosages will range from about 0.01 to about 1.0 MMol of paramagnetic ion complex per kg of patient body weight. Preferred parenteral dosages range from about 0.05 to about 0.5 MMol of paramagnetic ion complex per kg of patient body weight. Enteral dosages generally range from about 0.5 to about 100 MMol, preferably from about 1.0 to about 20 MMol of paramagnetic ion complex per kg of patient body weight.

The novel NMR image contrasting agents of this invention possess a unique combination of desirable features. The paramagnetic ion complexes exhibit an unexpectedly high solubility in physiological fluids, notwithstanding their substantially non-ionic character. This high solubility allows the preparation of concentrated solutions, thus minimizing the amount of fluid required to be administered. The non-ionic character of the complexes also reduces the osmolarity of the diagnostic compositions, thus preventing undesired edema and other side effects. As illustrated by the data presented below, the compositions of this invention have very low toxicities, as reflected by their high $LD_{50}$ values.

The diagnostic compositions of this invention are used in the conventional manner. The compositions may be administered to a warm-blooded animal either systemically or locally to the organ or tissue to be imaged, and the animal then subjected to the NMR imaging procedure. The compositions have been found to enhance the magnetic resonance images obtained by these procedures. In addition to their utility in magnetic resonance imaging procedures, the complexing agents of this invention may also be employed for delivery of radiopharmaceuticals or heavy metals for x-ray contrast into the body.

The invention is further illustrated by the following examples, which are not intended to be limiting.

EXAMPLE I

Preparation of
N,N''-Bis[N-(2-methoxyethyl)-carbamoylmethyl]diethylenetriamine-N,N',N''-triacetic acid.

A stirred suspension of DTPA-dianhydride (10.8 g, 0.030 mole) in 100 ml. of isopropanol was treated with 2-methoxyethylamine (5.0 g, 0.067 mole). The entire mixture was heated at 50° C. for 4 hours in a water bath. The pale yellow solution was filtered through a medium porosity sintered glass funnel to remove undissolved impurities, and the filtrate was taken to dryness under reduced pressure. The resulting amorphous foam was dried (vacuum desiccator) at ambient temperature for 18 hours. The yield of the bis(2-methoxyethylamide) of DTPA was 14.4 g (93.5%). $^{12}$C-NMR (22.49 MHz, D$_2$O, ref. p-dioxane at δ67.4): δ173.5, 172.3, 170.4, 71.0, 58.8, 57.9, 57.5, 55.9, 52.4, 52.1, 39.6. Analysis calculated for $C_{20}H_{37}N_5O_{10}\cdot 0.4H_2O$: C, 46.67%; H, 7.25%; N, 13.61%. Found: C, 47.15%; H, 7.42%; N, 13.35%.

EXAMPLE II

Preparation of
{N,N''-Bis[N-(2-methoxyethyl)-carbamoylmethyl]diethylenetriamine-N,N',N''-triaceto}gadolinium (III)

A mixture of gadolinium (III) oxide (3.3 g, 0.0091 mole) and bis(2-methoxyethylamide) of DTPA produced by the procedure described in Example I (10.2 g, 0.020 mole) in $H_2O$ (100 ml.) was heated at 60–65° C. for 3 hours in a water bath. The pale yellow homogeneous solution was filtered through a fine porosity sintered glass funnel to remove undissolved impurities and the clear filtrate was poured into acetone (2L). The heterogeneous mixture was stirred for 5 minutes and allowed to stand at ambient temperature for 30 minutes. Aqueous acetone was decanted off and the resulting gummy residue was dissolved with methanol (150 ml.). The solution was concentrated under reduced pressure and the complex was precipitated from the solution by adding it to more acetone (1L). The amorphous precipitate was collected, washed with acetone (2×100 ml.) and dried. The yield was 11.2 g (80.7%). The pale cream solid was crystallized from a mixture of methanol and tetrahydrofuran to give a colorless solid. It was 97.4% pure by HPLC. Analysis calculated for $C_{20}H_{34}N_5O_{10}Gd \cdot 1.4\ H_2O$: C, 34.95%; H, 5.41%; N, 10.19%; Gd, 22.88%. Found: C, 35.20%; H, 5.42%;, N, 10.27%; Gd, 22.52%.

EXAMPLE III

Preparation of
N,N''-Bis[N-(2-ethoxyethyl)carbamoyl-methyl]diethylenetriamine-N,N',N''-triacetic acid.

The procedure of Example I is repeated in all essential details, except that ethoxyethylamine (5.97 g, 0.067 mole) is substituted for methoxyethylamine. The procedure produces the title compound in good yield.

EXAMPLE IV

Preparation of
{N,N''-Bis[N-(2-ethoxyethyl)-carbamoylmethyl]diethylenetriamine-N,N',N''-triaceto}gadolinium (III)

The procedure of Example II is repeated in all essential details, except that the bis(2-ethoxyethylamide) of DTPA produced by the procedure described in Example V is substituted in equimolar amount for the bis(2-methoxyethylamide) of DTPA. The procedure produces the title compound in good yield.

EXAMPLE V

Preparation of
{N,N''-Bis[N-(2-methoxyethyl)-carbamoylmethyl]diethylenetriamine-N,N',N''-triaceto} iron (III)

The procedure of Example II is repeated in all essential details, except that iron (III) acetylacetonate is substituted in equimolar amount for gadolinium (III) oxide. The procedure produces the title compound in good yield.

EXAMPLE VI

Preparation of
{N,N''-Bis[N-(2-methoxyethyl)-carbamoylmethyl]diethylenetriamine-N,N',N''-triaceto} Holmium (III)

The procedure of Example II is repeated in all essential details, except that holmium (III) oxide is substituted in equimolar amount for gadolinium (III) oxide. The procedure produces the title compound in good yield.

EXAMPLE VII

Preparation of N,N',N''-Tris[N-(2-methoxyethyl) carbamoylmethyl]-diethylenetriamine-N,N''-diacetic Acid DTPA (1 mol) is dissolved in acetonitrile by adding triethylamine (5 mol) and heating. The solution is cooled to room temperature. While stirring, isobutylchloroformate (3 mol) is added dropwise to this solution. An excess of 2-methoxyethylamine (7 mol) is added immediately and the reaction mixture is stirred until the reaction is complete. The solution is taken to dryness under reduced pressure. The crude product is purified by chromatography on an anion exchange column.

EXAMPLE VIII

Preparation of
{N,N',N''-Tris[N-(2-methoxyethyl)carbamoylmethyl]-diethylenetriamine-N,N''-diaceto} manganese(II)

An excess of the tris(2-methoxyethylamide) of DTPA produced by the procedure described in Example VII is dissolved in water and $MnCO_3$ is added. The mixture is stirred and heated until the solution becomes homogeneous. The solution is taken to dryness under reduced pressure to give the desired product.

EXAMPLE IX

Preparation of
N,N'-Bis[N-(2-methoxyethyl)carbamoyl-methyl] ethylenediamine-N,N'-diacetic Acid 2-Methoxyethylamine (3.0 g, 0.02 mol) in 100 ml of methanol was treated with EDTA-dianhydride (5.12 g, 0.02 mol). The reaction mixture was stirred for 5 hours and the solids dissolved. The solution was taken to dryness under reduced pressure. The residue was dried under high vacuum to give 8.5 g of glassy solid. Its $^{13}C$-NMR spectrum was consistent with the desired structure.

EXAMPLE X

Preparation of {N,N'-Bis[N-(2-methoxyethyl) carbamoyl-methyl]-ethylenediamine-N,N'-diaceto} manganese(II)

A 15% excess of the bis(2-methoxyethylamide) of EDTA produced by the procedure described in Example XI (1.1 g, 0.0026 mol) was dissolved in water (10 ml) and $MnCO_3$ (0.27 g, 0.0023 mol) was added. Upon warming for 30 minutes, the solution became homogeneous. The solution was taken to dryness under reduced pressure. The resulting glassy solid was very soluble in water.

EXAMPLE XI

The acute intravenous toxicity of the compound of Example II was determined as follows: ICR mice, at 1 to 4 per dose level, received single intravenous injections of the test substance via a lateral tail vein at the rate of approximately 1 ml/minute. The test substances were at concentrations chosen to result in dose volumes of 5 to 75 ml/kg body weight. Dosing began at a volume of 10 ml/kg. Dose adjustments up or down were made to closely bracket the estimated $LD_{50}$ with 4 animals per group (2 males and 2 females). Observations of the mice were recorded at times 0, 0.5, 1,2,4 and 24 hours and once daily thereafter for up to 7 days post injection. On the 7th day post injection, the mice were euthanized, weighed and necropsied. Abnormal tissues were noted. At this time a decision was made as to whether any histopathology was to be performed and whether or not the tissues should be retained. Necropsies were also performed on mice expiring after 24 hours post-injection, except for dead mice found on the weekends. The $LD_{50}$ values, along with 95% CI were calculated using a modified Behrens-Reed-Meunch method. The results for the complex of Example II are reported below:

$LD_{50}$: 22.5 mmol/kg

95% Confidence Limits: 17.4–29.0 mmol/kg

Sex and Weight Range of Mice: Males(18.0–20.3 g) Females (19.0–21.7 g).

The details of the test results are shown in Table I below. The data demonstrate that the complex of Example II was characterized by a low initial I.v. toxicity ($LD_{50}$ - 27mmol/kg) within the first 24 hours post injection. Two delayed deaths at 27.2 mmol/kg resulted in lowering the $LD_{50}$ to 22.5 mmol/kg. Surviving mice, in general, failed to gain weight during the 7-day post-injection period. Only one gross organ abnormality was noted at necropsy: a "pale" colored liver in a female dosed with 20.4 mmol/kg. No other mice at 20.4 mmol/kg or lower showed similar abnormalities. Thus, these preliminary tests suggest that the formulation has a low order of i.v. toxicity.

TABLE I

| Dose (mmol/kg) | Conc (M) | Immediate (0–1 hr) | Delayed (1–24 hr) | Delayed (1–7 days) | Total | Body Weight Change (g) |
|---|---|---|---|---|---|---|
| 6.8 | 0.68 | 0 | 0 | 0 | 0/2 | M: −1.1/F: +2.1 |
| 13.6 | 0.68 | 0 | 0 | 0 | 0/2 | M: +1.6/F: +1.4 |
| 20.4 | 0.68 | 1 | 0 | 0 | 1/4 | M: −1.1/F: −3.2 |
| 27.2 | 0.68 | 2 | 0 | 2 | 4/4 | — |
| 34.0 | 0.68 | 4 | — | — | 4/4 | — |

EXAMPLE XII $T_1$ and $T_2$ relaxivity curves of the complex of Example II were obtained using a RADX (10 megahertz) NMR analyzer. The RADX analyzer was thermally stabilized at 37° C. before performing any $T_1$ or $T_2$ measurements. Overall range tuning and mid-range calibration were performed on a 37° C. warmed $T_1$ standard at the beginning of the experiment, according to manufacturer's instructions. Subsequent to calibration, $T_1$ standards were tested to verify calibration and linearity.

Ten millimolar solutions of the complex were prepared in sterile water for injection ("SWFI") and in 4% human serum albumin ("HSA")/0.9% NaCl. A series of lower concentrations (0.25, 0.50, 1.0, 2.5 and 5.0 mM) were prepared to form a concentration curve. A sample of each prepared concentration was warmed to 37° C. in an NMR sample tube prior to assay. Triplicate $T_1$ and $T_2$ values were obtained on each dilution.

Separate linear regressions were determined using the reciprocal $T_1$ and $T_2$ mean values for the complex diluted in SWFI and 4% HSA. The relaxivity curves were generated by plotting the reciprocal $T_1$ or $T_2$ value against concentration. The following relaxation rates were determined for the complex of Example II:

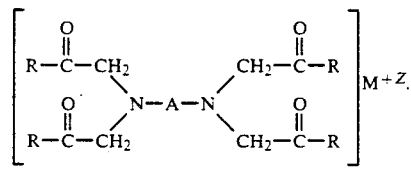

| Relaxation Rate (mM$^{-1}$ sec$^{-1}$) | | | |
|---|---|---|---|
| $T_1$ | | $T_2$ | |
| H$_2$O | HSA | H$_2$O | HSA |
| 4.69 | 4.40 | 4.81 | 6.38 |

I claim:

1. A complex having the following formula:

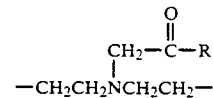

wherein A is selected from the group consisting of —CH$_2$ CH$_2$— and $$\begin{array}{c} \text{O} \\ \parallel \\ \text{CH}_2-\text{C}-\text{R} \\ | \\ -\text{CH}_2\text{CH}_2\text{NCH}_2\text{CH}_2- \end{array}$$

wherein M$^{+z}$ is a paramagnetic ion of an element with an atomic number of 21–29, 42–44 or 58–70, and a valence, Z, of 2 or 3; the R groups may be the same or different and are selected from the group consisting of —O$^\ominus$ and lower alkoxyalkylamino groups having from 2 to about 6 carbon atoms, the number of R groups —O$^\ominus$ equals Z and the remaining R groups are lower alkoxyalkylamino, equal to 4- Z when A is —CH$_2$CH$_2$—, or 5 - Z when Z is

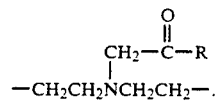

2. The complex of claim 1, wherein A is

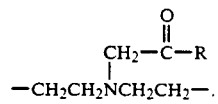

3. The complex of claim 1, wherein A is —CH$_2$CH$_2$—.

4. The complex of claim 2 or 3, wherein R is an alkoxyalkylamino, wherein the alkoxy portions contains 1 or 2 carbon atoms and the alkyl portion contains from about 2 to about 5 carbon atoms.

5. The complex of claim 2 or 3 wherein R is methoxyethylamino, methoxypropylamino, methoxybutylamino, methoxypentylamino, ethoxyethylamino, ethoxypropylamino or ethoxybutylamino.

6. The complex of claim 4, wherein $M^{+z}$ is chromium (III), manganese (II), manganese (III), iron (III), iron (II), cobalt (II), nickel (II), copper (II), praseodymium (III), neodymium (III), samarium (III), ytterbium (III), gadolinium (III), terbium (III), dysprosium (III), holmium (III) or erbium (III).

7. The complex of claim 5, wherein $M^{+z}$ is gadolinium (III), terbium (III), dysprosium (III), holmium (III) or erbium (III).

8. The complex of claim 2, wherein R is methoxyethylamino and $M^{+z}$ is gadolinium (III).

9. A diagnositc composition suitable for enteral or parenteral administration to a warm-blooded animal, which comprises an NMR imaging-effective amount of a complex of a paramagnetic ion having the following formula:

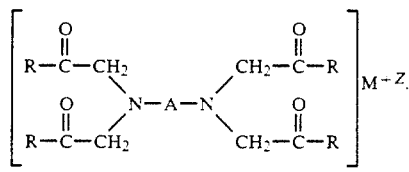

wherein A is selected from the group consisting of —$CH_2CH_2$— and

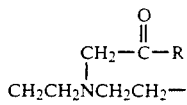

wherein $M^{+z}$ is a paramagnetic ion of an element with an atomic number of 21-29, 42-44 or 58-70, and a valence, Z, of 2 or 3; the R groups may be the same or different and are selected from the group consisting of —$O^\ominus$ and lower alkoxyalkylamino groups having from 2 to about 6 carbon atoms, the number of R groups —$O^\ominus$ equals Z and the remaining R groups are lower alkoxyalkylamino, equal to 4-Z when A is —$CH_2CH_2$—, or 5-Z when Z is

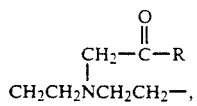

and a pharmaceutically acceptable carrier.

10. The composition of claim 9, wherein A is

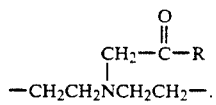

11. The composition of claim 9, wherein A is —$CH_2CH_2$—.

12. The composition of claim 10 or 11, which is suitable for parenteral administration, wherein R is an alkoxyalkylamino, in which the alkoxy portions contains 1 or 2 carbon atoms and the alkyl portion contains from about 2 to about 5 carbon atoms, and the complex is dissolved or suspended in a sterile aqueous pharmaceutically acceptable carrier at a concentration of from about 0.05 to 1.0M.

13. The composition of claim 12, wherein R is methoxypropylamino, methoxybutylamino, methoxyethylamino, ethoxyethylamino, methoxypentylamino, ethoxypropylamino or ethoxybutylamino, and wherein the concentration of the complex in the composition is from about 0.05 to about 1.0M.

14. The composition of claim 13, wherein $M^{+z}$ is chromium (III), manganese (II), manganese (III), iron (III), iron (II), cobalt (II), nickel (II), copper (II), praseodymium (III), neodymium (III), samarium (III), ytterbium (III), gadolinium (III), terbium (III), dysprosium (III), holmium (III) or erbium (III).

15. The composition of claim 13, wherein $M^{+z}$ is gadolinium (III), terbium (III), dysprosium (III), holmium (III) or erbium (III).

16. The composition of claim 15, wherein R is methoxyethylamino and $M^{+z}$ is gadolinium (III).

17. The composition of claim 13, which further contains a pharmaceutically acceptable buffer.

18. The composition of claim 12, which further contains a pharmaceutically acceptable electrolyte.

19. The composition of claim 11, which further comprises a stoichiometric excess of a complexing agent of the formula

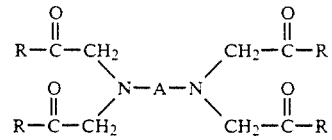

wherein A and R are as defined as in claim 11.

20. The composition of claim 19, wherein said excess complexing agent is complexed with a physiologically acceptable, non-toxic cation.

21. The composition of claim 20, wherein said excess complexing agent is employed in an amount ranging from about 0.1 to about 15 mole % excess, relative to the paramagnetic ion, and is complexed with a cation selected from the group consisting of calcium ions, magnesium ions, copper ions and zinc ions.

22. The composition of claim 21, wherein said excess complexing agent is complexed with calcium ions.

23. A method of performing an NMR diagnostic procedure, which comprises administering to a warm-blooded animal an effective amount of a complex of the formula

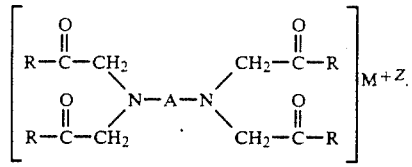

wherein A is selected from the group consisting of

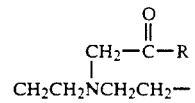

wherein $M^{+z}$ is a paramagnetic ion of an element with an atomic number of 21-29, 42-44 or 58-70, and a valence, Z, of 2 or 3; the R groups may be the same or different and are selected from the group consisting of —O$^\ominus$ and lower alkoxyalkylamino groups having from 2 to about 6 carbon atoms, wherein the number of R groups —O$^\ominus$ equals Z and the remaining R groups are lower alkoxyalkylamino, equal to 4-Z when A is —CH$_2$CH$_2$—, or 5-Z when A is

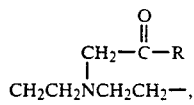

and then exposing the animal to an NMR imaging procedure, thereby imaging at least a portion of the body of the warm-blooded anmial.

24. The method of claim 23, wherein A is

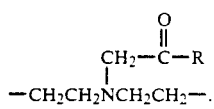

25. The method of claim 23, wherein A is -CH$_2$CH$_2$—.

26. The method of claim 24 or 25, wherein the complex is administered parenterally and wherein R is an alkoxyalkylamino, in which the alkoxy portions contains 1 or 2 carbon atoms and the alkyl portion contains from about 2 to about 5 carbon atoms, and the complex is dissolved or suspended in a sterile aqueous pharmaceutically acceptable carrier at a concentration of from about 0.05 to 1.0M.

27. The method of claim 26, wherein R is methoxypropylamino, methoxybutylamino, methoxyethylamino, ethoxyethylamino, methoxypentylamino, ethoxypropylamino or ethoxybutylamino, and wherein the concentration of the complex in the pharmaceutically acceptable carrier is from about 0.05 to about 1.0M.

28. The method of claim 27, wherein M$^{+z}$ is chromium (III), manganese (II), manganese (III), iron (III), iron (II), cobalt (II), nickel (II), copper (II), praseodymium (III), neodymium (III), samarium (III), ytterbium (III), gadolinium (III), terbium (III), dysprosium (III), holmium (III) or erbium (III).

29. The method of claim 27, wherein M$^{+z}$ is gadolinium (III), terbium (III), dysprosium (III), holmium (III) or erbium (III).

30. The method of claim 27, wherein R is methoxyethylamino and M$^{+z}$ is gadolinium (III).

31. The method of claim 27, wherein the pharmaceutically acceptable carrier contains a pharmaceutically acceptable buffer.

32. The method of claim 27, wherein the pharmaceutically acceptable carrier contains a pharmaceutically acceptable electrolyte.

33. The method of claim 27, wherein the pharmaceutically acceptable carrier contains a stoichiometric excess of a complexing agent of the formula

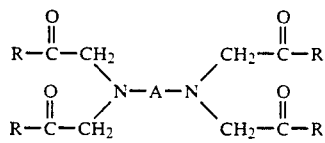

wherein A and R are as defined as in claim 27.

34. The method of claim 33, wherein said excess complexing agent is complexed with a physiologically acceptable, non-toxic cation.

35. The method of claim 34, wherein said excess complexing agent is employed in an amount ranging from about 0.1 to about 15 mole % excess, relative to the paramagnetic ion, and is complexed with a cation selected from the group consisting of calcium ions, magnesium ions, copper ions and zinc ions.

36. The method of claim 35, wherein said excess complexing agent is complexed with calcium ions.

37. A complexing agent of the formula:

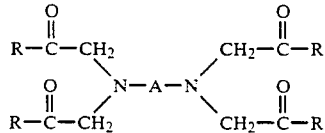

wherein A is selected from the group consisting of —CH$_2$CH$_2$— and

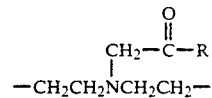

wherein the complexing agent has a valence, Z, of 2 or 3; the R groups may be the same or different and are selected from the group consisting of —O$^\ominus$ and lower alkoxyalkylamino groups having from 3 to about 6 carbon atoms, wherein the number R groups —O$^\ominus$ equals Z and the remaining R groups are lower alkoxyalkylamino, equal to 4-Z when A is —CH$_2$CH$_2$—, or 5-Z when Z is

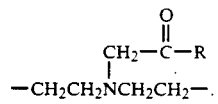

38. The complexing agent of claim 37, wherein A is

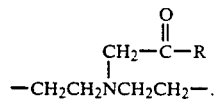

39. The complexing agent of claim 37, wherein A is —CH$_2$CH$_2$—.

40. The complexing agent of claim 38 or 39, wherein R is an alkoxyalkylamino, in which the alkoxy portions contains 1 or 2 carbon atoms and the alkyl portion contains from about 2 to about 5 carbon atoms.

41. The complexing agent of claim 40, wherein R is methoxyethylamino, methoxypropylamino, methoxybutylamino, methoxypentylamino, ethoxyethylamino, ethoxypropylamino or ethoxybutylamino.

* * * * *

UNITED STATES PATENT AND TRADEMARK OFFICE
CERTIFICATE OF CORRECTION

PATENT NO. : 5,130,120

DATED : July 14, 1992

INVENTOR(S) : Robert W. Weber

It is certified that error appears in the above-indentified patent and that said Letters Patent is hereby corrected as shown below:

On the Cover, in the Abstract, before the last formula insert --is--.

Col. 6, line 64 "$^{12}C-NMR$" should be --$^{13}C-NMR$--.

Signed and Sealed this

Twenty-eighth Day of December, 1993

Attest:

BRUCE LEHMAN

Attesting Officer     *Commissioner of Patents and Trademarks*